United States Patent
McCallum et al.

(10) Patent No.: US 12,254,976 B2
(45) Date of Patent: Mar. 18, 2025

(54) HEALTHCARE CLINICAL EFFICIENCY CLAIMS PER HEALTHY DAY NAVIGATION ENGINE

(71) Applicant: Integer Health Technologies, LLC, Arlington, TX (US)

(72) Inventors: Jack McCallum, Benbrook, TX (US); Scott Roloff, Arlington, TX (US); William McCallum, Fort Worth, TX (US); Ken Grifno, The Colony, TX (US)

(73) Assignee: Integer Health Technologies, LLC, Arlington, TX (US)

( * ) Notice: Subject to any disclaimer, the term of this patent is extended or adjusted under 35 U.S.C. 154(b) by 255 days.

(21) Appl. No.: 17/968,296

(22) Filed: Oct. 18, 2022

(65) Prior Publication Data

US 2023/0123221 A1 Apr. 20, 2023

Related U.S. Application Data

(63) Continuation-in-part of application No. 16/031,559, filed on Jul. 10, 2018, now abandoned.

(51) Int. Cl.
*G16H 40/20* (2018.01)
*G06F 16/2457* (2019.01)

(52) U.S. Cl.
CPC ....... *G16H 40/20* (2018.01); *G06F 16/24578* (2019.01)

(58) Field of Classification Search
CPC ........ G16H 40/20; G16H 50/30; G06Q 10/10; G06N 3/08; G06F 16/9535; G06F 16/316
See application file for complete search history.

(56) References Cited

U.S. PATENT DOCUMENTS

2012/0116985 A1* 5/2012 Rastogi ................ G06Q 30/018
705/347
2015/0073943 A1 3/2015 Norris et al.
(Continued)

OTHER PUBLICATIONS

Integer Health, QScore (WayBack Machine capture Aug. 16, 2016) (Year: 2016).*

(Continued)

*Primary Examiner* — Jordan L Jackson
(74) *Attorney, Agent, or Firm* — Vincent J. Allen; James H. Ortega; Carstens, Allen & Gourley, LLP (57) ABSTRACT

A navigation engine for medical and/or pharmacy claims (in combination with employer human resource records or on a stand-alone basis) that quantifies healthcare outcomes and ranks healthcare providers and other healthcare items by root diagnosis based on their overall average claims per healthy day (i.e., clinical efficiency). Claims per healthy day is the adjusted claims cost per day to keep a patient healthy (or in the case of an employer, keep an employee at work), so the lower, the better. The navigation engine uses drop-down menus and/or similar techniques that require the user to select a root diagnosis on which to search, as well as other variables (e.g., provider category, geographic proximity, in-network versus in or out of network, etc.), turning an open-ended question, e.g., "Which doctor should I go to for back pain?" to a closed-ended one "Which surgeons in my network within 25 miles have the best outcomes for back surgery?"

18 Claims, 8 Drawing Sheets

Navigation Engine's Visual Display (56) References Cited

U.S. PATENT DOCUMENTS

2017/0053080 A1     2/2017   Geppert et al.
2019/0371450 A1    12/2019   Lou et al.

OTHER PUBLICATIONS

Brantes, Measuring Provider Efficiency Version 1.0, The Leapfrog Group & Bridges To Excellence 1-51 (Dec. 31, 2004) (Year: 2004).*
Hileman et al., Risk Scoring in Health Insurance: A Primer, Society of Actuaries (Year: 2016).*
Worthington, Frontier Efficiency Measurement in Healthcare: A Review of Empirical Techniques and Selected Application, 61(2) Medical Care Research and Review 1-36 (Year: 2004).*
Pienta et al., VISAGE: Interactive Visual Graph Querying, AVI '16: Proceedings of the International Working Conference on Advanced Visual Interfaces 272-279 (Year: 2016).*
Cocitation Network Graph, Signs at 40 Sings Journal (screen reproduction from Nov. 2, 2014) (Year: 2014).*
Stack Overflow question "Display node information(other custom information) when i hover/click over a node in Graphviz in python" (Year: 2017).*
Graphviz, Graph Visualization Software (Year: 2016).*
A.D. Dongare et al., Introduction to Artifical Neural Network, 2(1) International Journal of Engineering and Innovative Technology 189-194 (Year: 2012).
Jordan and Mitchell, Machine Learning: Trends, Perspectives, and Prospects, 349(6245) Science 255-260 (Jul. 17, 2015) (Year: 2015).

\* cited by examiner

Claims per Healthy Day Math

HEALTHCARE CLINICAL EFFICIENCY CLAIMS PER HEALTHY DAY NAVIGATION ENGINE

RELATED APPLICATIONS

The present disclosure is a continuation-in-part application of U.S. patent application Ser. No. 16/031,559, filed Jul. 10, 2018. Additionally, this disclosure is related to commonly-owned U.S. patent application Ser. No. 17/864,631, filed Jul. 14, 2022, which is a CIP of U.S. patent application Ser. No. 15/225,503, filed Aug. 1, 2016, which claims the benefit of U.S. Patent App. No. 62/387,534, filed Dec. 28, 2015; U.S. patent application Ser. No. 15/950,681, filed Apr. 11, 2018; and U.S. patent application Ser. No. 17/855,694, filed Jun. 30, 2022; all of which are incorporated by reference herein in their entireties.

TECHNICAL FIELD

The invention is a computer navigation engine that quantifies healthcare outcomes in dollars and cents based upon their risk-adjusted claims per healthy day-sometimes referred to as clinical efficiency or outcome efficiency. Quantifying healthcare outcomes permits ranking healthcare items by the outcomes that they achieved, such as physicians and other providers, facilities, case managers, workers' compensation adjusters, healthcare treatment patterns and/or practices, healthcare plans and/or programs and provider networks, etc. (collectively, "Healthcare Items"), and calculating returns on investment.

BACKGROUND

Medical and pharmacy claims—the input into the healthcare equation—are measured in dollars and cents. Until now the output-what is received in exchange for those healthcare dollars—has been measured in qualitative terms, such as what a provider did or didn't do (compliance with HEDIS and clinical guideline checklists) and whether the patient "liked" the doctor or healthcare experience (scored by CAHPS and Press Ganey).

What is needed is a way to quantify the output—the patient's outcome—in dollars and cents too so that the inputs and outputs are in the same terms, enabling the ranking of Healthcare Items based on the outcomes that they achieved and the calculating of ROIs (Returns on Investment).

SUMMARY

The invention is a navigation engine that quantifies healthcare outcomes based on their risk-adjusted claims per healthy day during a year (or other period), combining cost and quality into a single dollar and cent value.

The claims measure the cost of the healthcare, while the healthy days measure the quality.

BRIEF DESCRIPTION OF THE DRAWINGS

A complete understanding of this invention may be obtained by reference to the accompanying drawings in conjunction with the following detailed description.

DETAILED DESCRIPTION

Various objects, features, aspects and advantages will become apparent from the following detailed description along with the accompanying drawings. The principles are described with specificity. This description and the drawings, however, are not intended to limit the scope of the principles disclosed herein. These principles might also be embodied in other ways and include different steps or combinations of steps similar to the ones described.

This invention is a navigation engine for medical and pharmacy claims data that quantifies healthcare outcomes in dollars and cents based on the risk-adjusted claims per healthy day.

Figure 1:
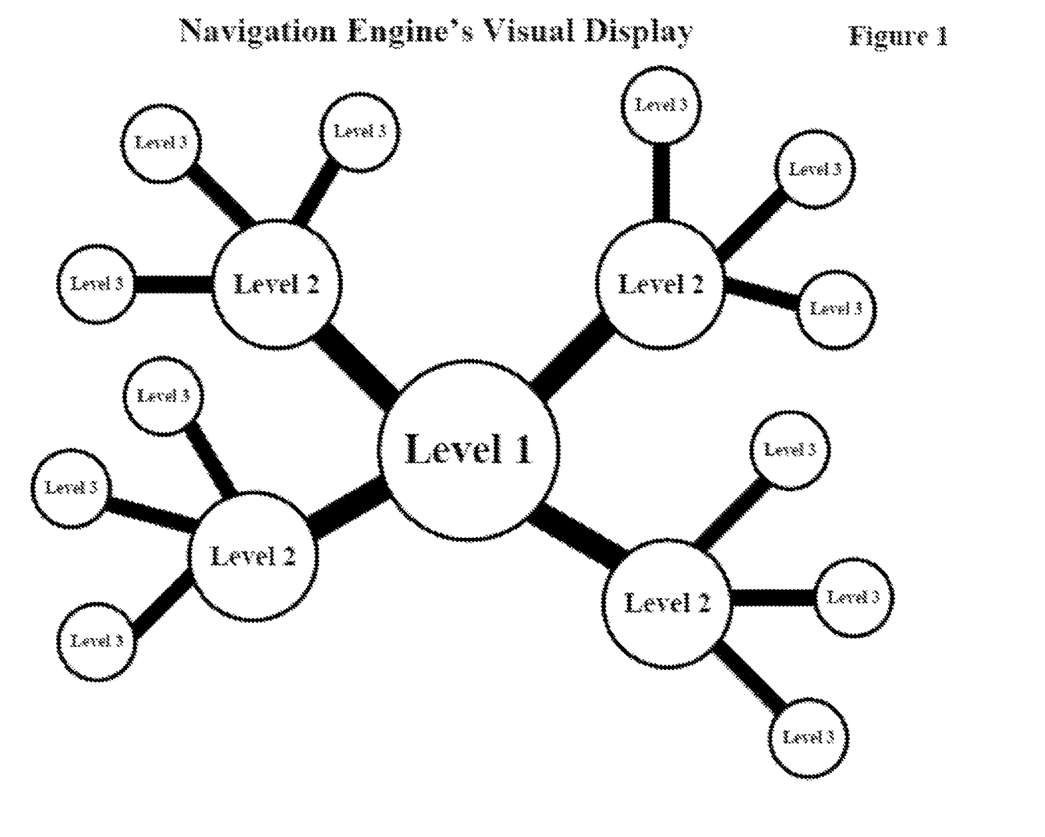
FIG. 1 shows how the navigation engine visually displays all the data on the computer monitor at one time, arranging the data into categories and sub-categories for easy retrieval by hoovering the computer mouse's curser over the desired data and clicking on it.

The navigation engine is deployed on a computer connected to a computer monitor and computer mouse. As shown in FIG. 1, the engine employs the novel approach of representing categories and sub-categories of material with functionally labeled circles connected in a hierarchical organization on a single computer screen. Descending circles in the hierarchy represent more detailed subsets of the material. Hovering the computer mouse over a circle displays thumbnails of the dashboards and reports available under it. For example, one category may be physicians, with sub-categories for primary care physicians (PCPs), specialists and surgeons. Another category may be diagnoses, with sub-categories for chronic versus episodic conditions, and then individual diagnoses under each.

The navigation engine visually displays all the data on the computer monitor at one time, arranging the data into categories and sub-categories for easy retrieval. Hovering the computer mouse over a circle displays thumbnails of the dashboards and reports available under it. The user can click on a circle with the computer mouse to open that category, or click on a thumbnail to access a dashboard or report directly. For example, Level 1 may be an umbrella dashboard or report. One Level 2 may then break the data down to physicians, and the connected Level 3s by physician type (e.g., PCPs, Specialists & Surgeons), while a second Level 2 breaks the data down by diagnoses, with the connected Level 3s by diagnosis type (e.g., chronic versus episodic), and then Level 4s (not shown) by individual diagnoses.

This navigation technology improves the computer's functionality by transforming the literal display of data into a visual one on a single computer screen; thereby improving computer and network performance by decreasing the resources used to open and close screens while searching for the right one, while increasing the effectiveness and speed of the user's search process.

This navigation engine can be deployed only on claims data, or on claims data in combination with employer human resource records. When the navigation engine uses both claims and human resource records, the results reported concern only the employees of the employer, not any other individuals covered under the employer's health plan.

To increase the number of claims and produce more robust results the claims from different plans, employers and/or sources can be pooled.

The navigation engine displays different results depending on the user.

In each case, the navigation engine uses drop-down menus and/or similar techniques that require the user to select a root diagnosis on which to search, as well as other variables (e.g., provider category, in-network versus in or out of network, geographic proximity, etc.). For example, when searching for a doctor the navigation engine turns an open-ended question, "Which doctor should I go to for back pain?" to a closed-ended one "Which surgeons in my network within 25 miles have the best outcomes for back surgery?"

If the user is a health plan, provider network, employer, or other administrative user, the navigation engine displays the overall average claims per heathy day by root diagnosis of each Healthcare Item in the category being measured, including configurations and subsets in various dashboards and reports.

If the user is a PCP or other physician, case manager, workers' compensation adjuster, or other healthcare provider that needs to make a patient referral or choose from several available treatment patterns and/or practices, the navigation engine displays the overall average claims per healthy day by root diagnosis of the healthcare specialists, surgeons and institutions treating patients with that diagnosis that have an overall average claims per healthy day better than or equal to a designated threshold and/or an overall average claims per healthy day of the possible treatment patterns and/or practices better than a designated threshold. For example, if the navigation engine is set to display only specialists, surgeons and institutions whose overall average claims per healthy day is better than the average for that category, the engine will only display those providers whose overall average claims per healthy day is better than that average (i.e., lower because the claims per healthy day is the adjusted claims cost per day to keep a patient healthy, so the lower the cost the better).

If the user is an individual seeking treatment, the navigation engine displays the overall average claims per healthy day by root diagnosis of all healthcare providers (e.g., PCPs, specialists, surgeons and healthcare institutions) treating patients with that diagnosis that have an overall average claims per healthy day better than or equal to the designated threshold. In this scenario the navigation engine could also display the overall average claims per healthy day of the possible treatment patterns and/or practices, but may not do so because individuals without a medical background may not have the experience required to interpret the results.

In addition to (or in replacement of) the overall average claims per healthy day displayed to PCPs and other healthcare providers needing to make referrals, or choose from several treatment patterns and/or practices, as well as individuals seeking treatment, the navigation engine can display the predicted claims per heathy day for a provider when treating a particular patient, or for a particular treatment pattern and/or practice, by taking the overall average claims per healthy day for the provider or treatment pattern and multiplying it by the individual's risk score, and if the individual is an employee, then multiplying the resulting product by the employee's job factor too (before or after the risk score and job factor are modified through the regression analysis and neural network and machine learning loop described below).

Figure 2:
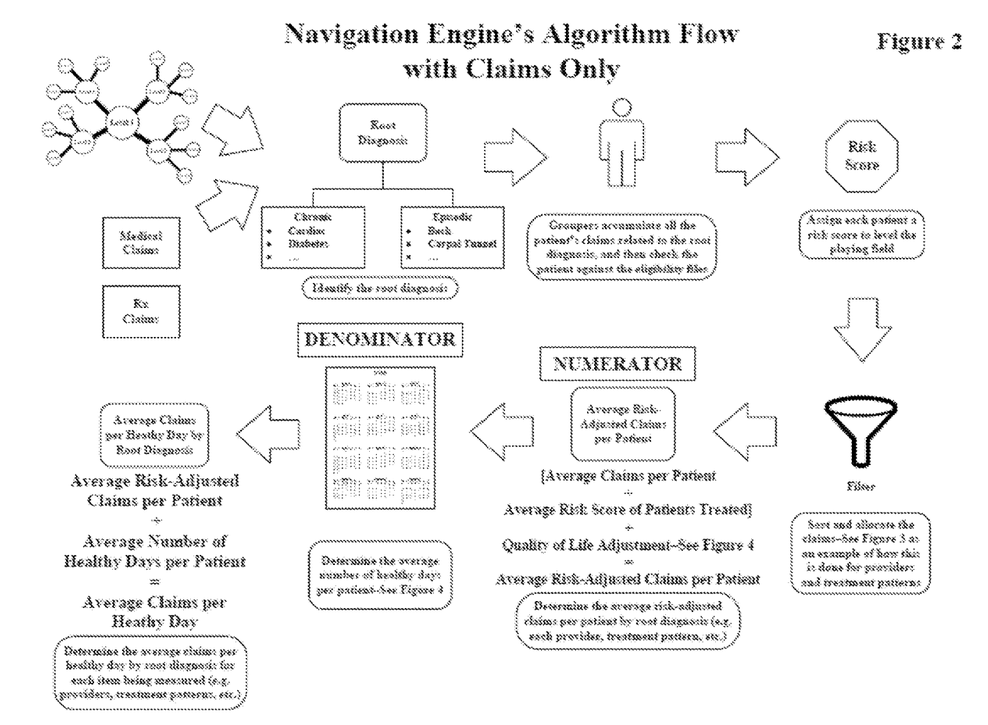
FIG. 2 walks through the navigation engine's flow from the visual interface at the beginning to the quantified healthcare outcome at the end when using medical and pharmacy claims only, with a cut-out for sorting and allocating the claims by both provider and treatment pattern, which is shown in FIG. 3, and a cut-out for determining a patient's healthy days and the quality of life adjustment, which is shown in FIG. 4. This drawing depicts quantifying the outcomes achieved by physicians only as an example. The invention can quantify the outcomes for any Healthcare Item.
Figure 3:
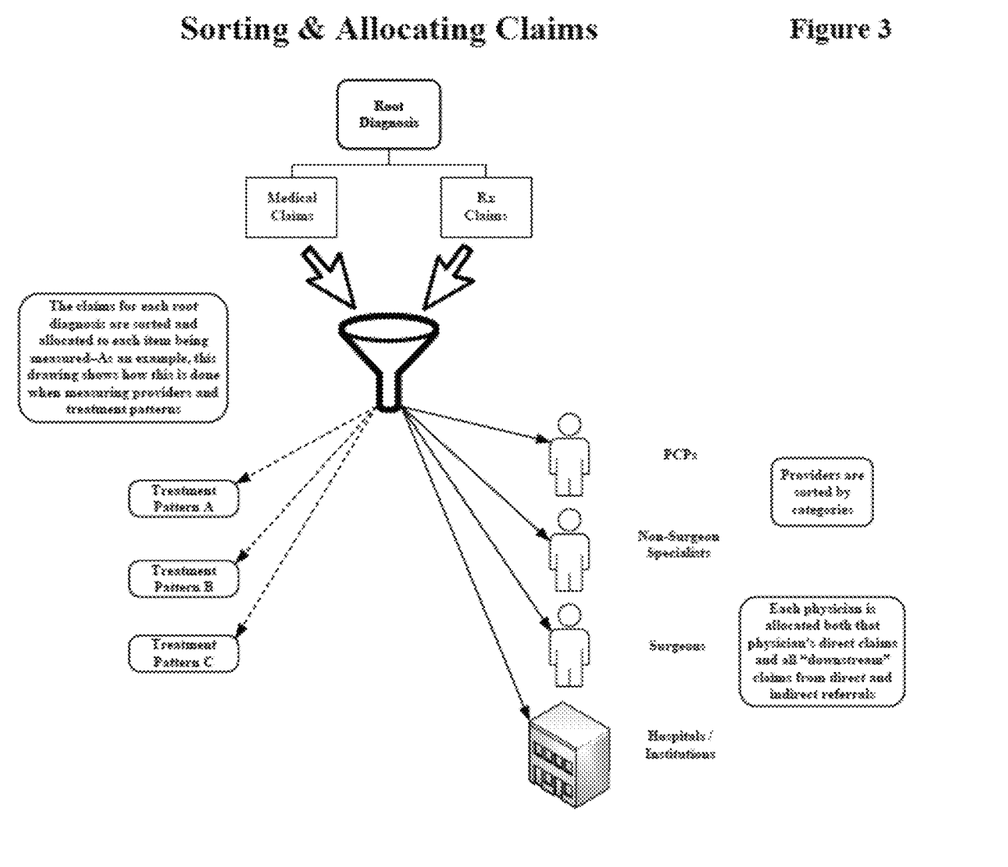
FIG. 3 shows the navigation engine's flow for sorting and allocating the claims by both provider and treatment pattern.
Figure 4:
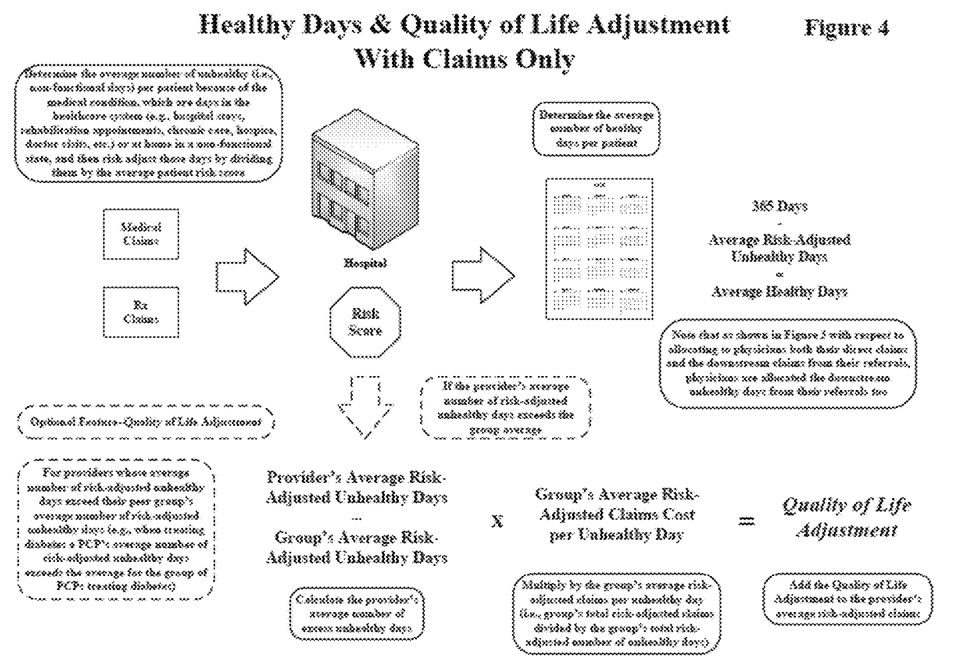
FIG. 4 shows the navigation engine's flow for determining a patient's healthy and unhealthy days when searching medical and pharmacy claims only, and then calculating the quality of life adjustment that may be used to separate further those providers keeping their patients healthy from those providers who are not.

FIG. 2 walks through the navigation engine's flow from the visual interface at the beginning to the quantified healthcare outcome at the end-Claims per Healthy Day. This drawing, along with FIGS. 3 & 4, depicts ranking physicians only as an example. The invention can quantify the outcomes for anything, e.g., physicians and other providers, facilities, case managers, workers' compensation adjusters, healthcare treatment patterns and/or practices, healthcare plans and/or programs and provider networks, etc. More specifically, FIG. 2 walks through the navigation engine's flow from the visual interface at the beginning to the quantified healthcare outcome at the end when using medical and pharmacy claims only, with a cut-out for sorting and allocating the claims by both provider and treatment pattern, which is shown in FIG. 3, and a cut-out for determining a patient's healthy days and the quality of life adjustment, which is shown in FIG. 4. This drawing depicts quantifying the outcomes achieved by physicians only as an example. The invention can quantify the outcomes for any Healthcare Item. The navigation engine works best when searching both medical and pharmacy claims, but can be used on just medical claims without pharmacy claims (and under certain circumstances, on just pharmacy claims without medical claims). This detailed description and the drawings assume deployment on both.

First, the navigation engine organizes the medical and pharmacy claims in tables with various headers that enable filtering, grouping and matching. The engine then sifts through all the claims and identifies the root diagnosis for each patient's claims (or root diagnoses, if more than one). A "root diagnosis" is the patient's main problem from which all related claims emanate. There are two main categories of root diagnoses: chronic conditions that seldom or never go away (e.g., cardiac problems, diabetes, etc.) and episodic conditions that may (e.g., back pain, carpal tunnel syndrome, etc.). Some episodic conditions may morph into chronic ones because they are not cured (e.g., back pain), while some episodic conditions should always have a beginning and an end (e.g. broken leg that heals). Under each main category there are many root diagnoses.

Next, the navigation engine's groupers accumulate all the medical and pharmacy claims attributable to a patient's root diagnosis.

The navigation engine then groups the claims by measurement period, such as an annual period (e.g., calendar years or rolling twelve-month periods). Under certain circumstances the navigation engine could use something other than an annual period. For example, the navigation engine could determine the average number of days for an episodic root diagnosis and use that average as the measurement period. The default measurement period, and the one assumed for the balance of this description and the drawings, is an annual period.

After that the navigation engine organizes the eligibility files for any applicable health plan or other program in tables with various headers that enable filtering, grouping and matching, and determines whether each patient participated in that plan or program for the entirety of each measurement period. The search engine may discard from the analysis patients to the extent that they only participate for part of a period.

The navigation engine then analyzes the claims to assign each patient a risk score denoting the patient's overall health. Any number of risk scoring systems may be used so long as they are demographically appropriate for the population. Risk scoring systems evaluate an individual's health based on several factors, which may include the individual's age, gender and comorbidities as determined by examining the individual's medical and pharmacy claims. Open-source risk-scoring systems include: HHS-HCC (Department of Health and Human Services-Hierarchical Condition Categories) designed for use in the Affordable Care Act marketplace (the sicker someone is the more the government pays the insurance company to insure them), CDPS (Chronic Illness & Disability Payment System) designed by the University of California at San Diego and used by many Medicaid programs, and CMS-HCC (Centers for Medicare & Medicaid Services-Hierarchical Condition Categories) used in connection with Medicare Advantage plans (as with HHS-HCC, the sicker the person is the more the government pays the plan to insure them). HHS-HCC and CDPS are appropriate for working age populations, while CMS-HCC is appropriate for retired ones. In addition, the engine may adjust the risk scores with certain social determinants of health (SDOH), and health plan/clinical data. SDOH include a person's ZIP code (which may indicate the person's access to healthy food) and compensation (which may indicate the person's ability to pay for healthcare). Health plan/clinical data include the type of health plan that the person has enrolled in (e.g., HMO-Health Maintenance Organization, PPO-Preferred Provider Organization or HDHP-High Deductible Health Plan) and clinical variables such as height, weight, and the results of any health assessments or evaluations.

The navigation engine normalizes the risk scores so that individuals of average health may receive a risk score of 1.000, individuals healthier than average a score below 1.000 (the lower the score, the healthier), and individuals sicker than average a score above 1.000 (the higher the score, the sicker). To further normalize the results, the navigation engine may assign a patient with a score of 1.000 or below a score of 1.000, while using the actual scores for individuals with scores above 1.000.

Next the navigation engine organizes the Healthcare Items whose outcomes are being analyzed in tables with various headers that enable filtering, grouping and matching.

When analyzing the outcomes for physicians, each physician is allocated both: (1) that physician's direct claims, and (2) all "downstream" claims from direct and indirect referrals of the patient made by that physician to other providers. Note that if all the claims costs of all the providers were added together that this would result in double, triple counting, etc., although for ranking purposes it doesn't matter. For example, if a PCP treated a patient and then referred that patient to a specialist, that PCP's claims would be not only the claims related to the PCP's treatment, but all the specialist's claims too. In addition, the specialist's claims would be attributed to the specialist, along with any downstream costs of further referrals (which would also be included in the PCP's costs). This attribution permits evaluation of referral patterns, which is essential when determining the outcomes that a provider achieves.

The navigation engine then sorts the Healthcare Items whose outcomes are being quantified into categories. For example, when evaluating physicians you cannot compare a PCP to a surgeon so the navigation engine might sort the providers into four categories: PCPs (including physician assistants and nurse practitioners), non-surgeon specialists, surgeons, and healthcare institutions (e.g., hospitals, outpatient centers, etc.). Similarly, the navigation engine could sort the claims by treatment pattern and/or practice, allocating to each treatment pattern and/or practice both the direct claims of that treatment pattern and/or practice and the indirect "downstream" claims stemming from it. Note that the navigation engine sorts the claims by any Healthcare Item whose outcomes are being quantified.

For each Healthcare Item whose outcome is being quantified the navigation engine then determines the risk-adjusted claims cost for each patient, by root diagnosis, for each measurement period, by taking the aggregate claims for that patient and diagnosis allocated to that item for that period, and dividing by the patient's risk score for that period. This risk adjustment gives credit for caring for sicker patients, who you would expect to cost more.

To obtain the total risk-adjusted claims for each root diagnosis for each Healthcare Item whose outcome is being quantified for each measurement period the navigation engine aggregates all the claims costs for that diagnosis allocated to that item for that period and divides that total by the average risk score for that period of the patients with that root diagnosis treated.

Next, the navigation engine determines the average claims per health day for each Healthcare Item whose outcome is being quantified for each measurement period for that root diagnosis by taking the total risk-adjusted claims costs for that diagnosis allocated to that item and dividing by the total healthy days in the measurement period of the patients treated.

As discussed above, the default measurement period is an annual period, so the total number of possible healthy days is 365.

To determine a patient's healthy days, the navigation engine begins by sifting through the claims and identifying each patient's unhealthy days related to a root diagnosis. An "unhealthy day" is a day when the patient was in the healthcare system or at home but not functioning according to the patient's normal activities because of that diagnosis. Examples of days in the healthcare system include days involving: in-patient hospital admissions, out-patient hospital admissions, in-patient rehabilitation, out-patient rehabilitation, in-patient chronic care, out-patient chronic care, hospice and doctor's visits.

As with the allocation of downstream claims back to a referring provider, a patient's unhealthy days after such a referral are also allocated back to the referring physician (as well as the provider referred to).

After that the navigation engine risk adjusts the patient's unhealthy days by dividing them by the patient's risk score.

A patient's healthy days are the total possible healthy days in the measurement period-365—less the risk-adjusted number of unhealthy days.

As with the claims, to obtain the total risk-adjusted unhealthy days for each root diagnosis for each Healthcare Item whose outcome is being quantified for each measurement period the navigation engine aggregates all the unhealthy days for that diagnosis allocated to that item for that period and divides that total by the average risk score for that period of the patients with that root diagnosis treated.

The "claims per health day" for a Healthcare Item whose outcomes are being quantified for a measurement period with respect to a patient with a particular root diagnosis is therefore the risk-adjusted claims cost allocated to that item with respect to that patient divided by that patient's healthy days. For example, take a patient with diabetes, a chronic root diagnosis. The PCP treating that patient is allocated $1,500 of claims costs during the year when treating that patient for that root diagnosis. The patient's risk score is 1.200, so the patient's risk-adjusted claims cost is $1,250 ($1,500÷1.200=$1,250). If the patient has 20 unhealthy days because of the diabetes, the risk-adjusted number of unhealthy days would be 17 (20÷1.200=17). The patient's healthy days would therefore be 348 (365−17=348). Accordingly, the PCP's claims per healthy day for treating this patient for diabetes would be $3.59 ($1,250÷348=$3.59). This is the cost per day to keep this patient healthy and functional.

The average claims per healthy day for a Healthcare Item whose outcomes are being quantified for a root diagnosis over a year would be the total claims cost of all the patients with that diagnosis allocated to that item during that period, divided by the average risk score of those patients during that period, and then divided by their total healthy days. When determining this average, outliers may be excluded, e.g., a patient on which the claims per healthy day is more than three standard deviations from the mean. In addition, items with less than a minimum number of patients may also be excluded. For example, assume that the PCP from the previous example treated ten patients during the year for diabetes and that the total claims costs allocated to the PCP was $19,500. The average risk score of the ten patients was 1.300, so the PCP's total risk-adjusted claims cost was $15,000 ($19,500÷1.300=$15,000), or $1,500 per patient ($15,000÷10=$1,500). If the ten patients had a total of 300 unhealthy days because of their diabetes, the risk-adjusted number of unhealthy days would be 231 (300÷1.300=231), or 23.1 per patient (231÷10=23.1). The total healthy days would therefore be 3,419 ((10×365)−231=3,419), or 341.9 per patient (3,419÷10=341.9). Accordingly, the PCP's average claims per healthy day for treating these ten patients for diabetes would be $4.39 ($15,000÷3,419=$4.39, or alternatively $1,500÷341.9=$4.39).

The navigation engine includes an optional "quality of life adjustment" that may be added to the average risk-adjusted claims cost, the numerator when calculating the claims per healthy day. When a Healthcare Item's average risk-adjusted unhealthy days exceed the average risk-adjusted unhealthy days of the peer group (the group of Healthcare Items whose outcomes are being quantified and ranked, e.g., PCPs treating diabetes, etc.), the excess risk-adjusted unhealthy days may be multiplied by the peer group's average risk-adjusted claims per unhealthy day, with the resulting amount added to the item's average risk-adjusted claims in the calculation. This quality of life adjustment provides greater separation of those in the peer group keeping patients healthy from those who are not. For example, continuing the example of the PCP treating ten patients with diabetes, the average number of risk-adjusted unhealthy days for those ten patients was 23.1 days. If the average for the peer group (all the PCPs treating patients with diabetes) was 20 days, then the excess number of risk-adjusted unhealthy days would be 3.1 (23.1−20=3.1). If the peer group's average risk-adjusted claims per patient were $1,450, then the peer group's average risk-adjusted claims per unhealthy day would be $72.50 ($1,450÷20=$72.50). The quality of life adjustment to be added to the subject PCP's average risk-adjusted claims would be $224.75 (3.1×$72.50=$224.75), increasing the PCP's claims per healthy day from $4.39 to $5.04 (($1,500+$224.75)÷341.9=$5.04).

When ranking Healthcare Items by root diagnosis, the navigation engine may use the overall average of the annual claims per healthy day for that diagnosis over several measurement periods of each item whose outcomes are being quantified and ranked using a simple average, weighted average or other means.

The navigation engine can also act on medical and pharmacy claims in combination with employer human resource records. In this scenario, outcome efficiency is determined on only employee data because there is no non-employee human resource data to match against the non-employees' medical and pharmacy claims. The claims per healthy day rankings derived from the employee data, however, can be used by employees and non-employees alike (e.g. spouses, dependent children, etc.) to identify the best providers and treatment patterns and/or practices for what they need, as well as by employers when directing care in connection with their workers' compensation programs. In addition, workers' compensation insurance companies and third-party administrators (TPAs) may use this approach by substituting the days missed from work because of an injury that they have in their systems for the employer's human resource records.

Alternatively, when using human resource records the navigation engine could take a bifurcated approach, determining the claims per healthy day with respect to the employees using those human resource records while determining the claims per healthy day with respect to the non-employees from only the claims data as discussed above.

Figure 5:
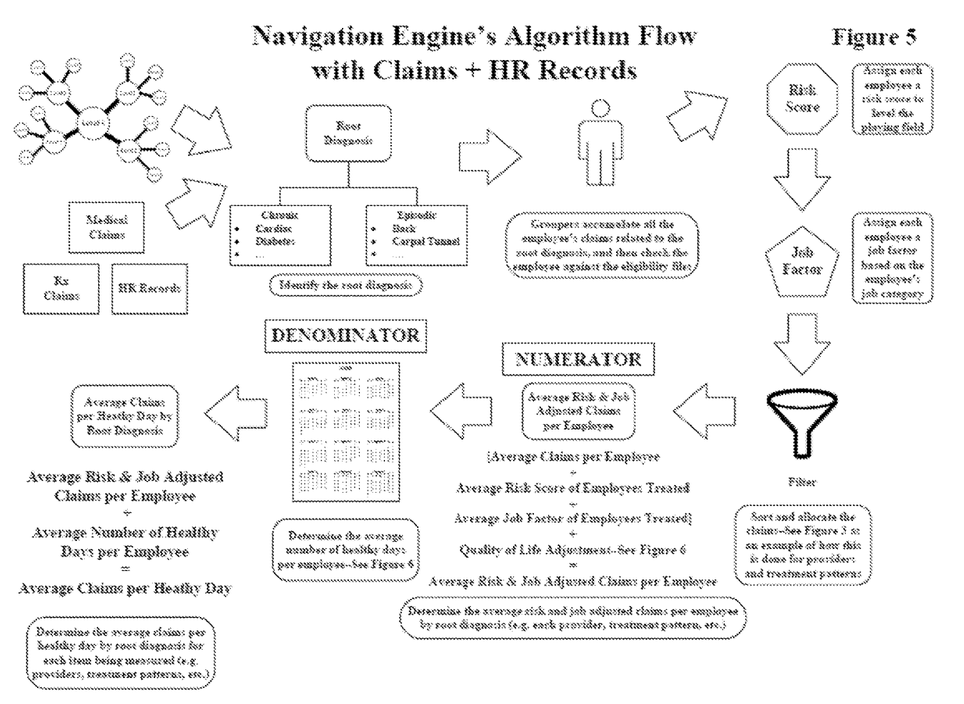
FIG. 5 walks through the navigation engine's flow from the visual interface at the beginning to the quantified healthcare outcome at the end when using medical and pharmacy claims in combination with employer human resource records, with a cut-out for sorting and allocating the claims by both provider and treatment pattern, which is shown in FIG. 3, and a cut-out for determining an employee's healthy days and the quality of life adjustment, which is shown in FIG. 6. This drawing depicts quantifying the outcomes achieved by physicians only as an example. The invention can quantify the outcomes for any Healthcare Item.
Figure 6:
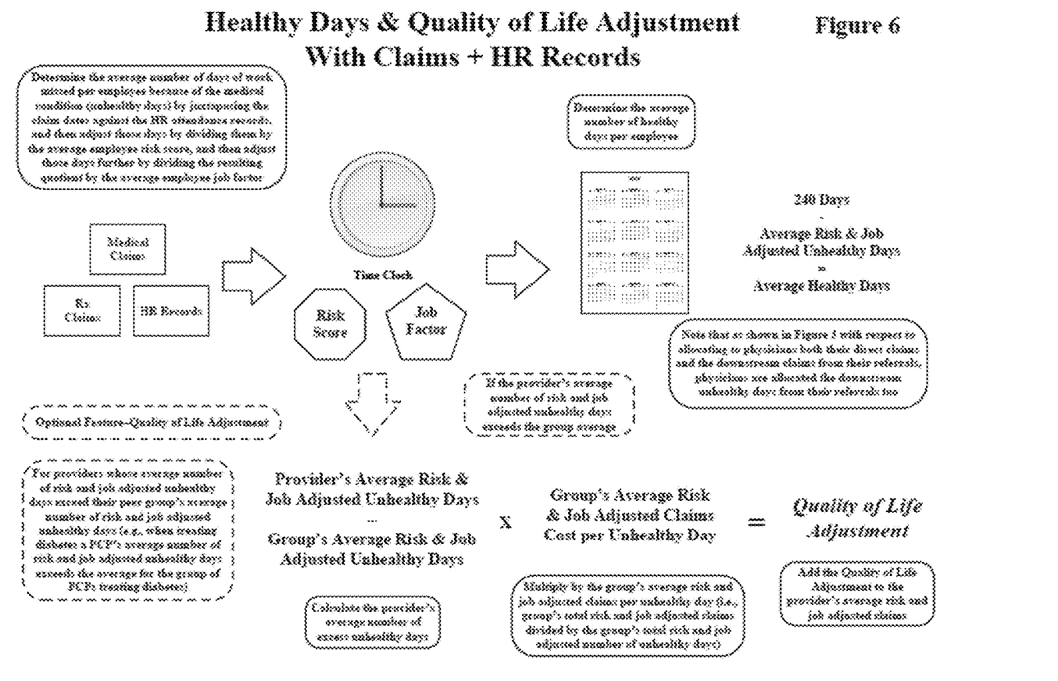
FIG. 6 shows the navigation engine's flow for determining an employee's healthy and unhealthy days when searching medical and pharmacy claims in combination with employer human resource records, and then calculating the quality of life adjustment that may be used to separate further those providers keeping their patients healthy from those providers who are not.

FIG. 5 walks through the navigation engine's flow from the visual interface at the beginning to the quantified healthcare outcome at the end-Claims per Healthy Day. This drawing, along with FIGS. 3 & 6, depicts ranking physicians only as an example. The invention can quantify the outcomes for anything, e.g., physicians and other providers, facilities, case managers, workers' compensation adjusters, healthcare treatment patterns and/or practices, healthcare plans and/or programs and provider networks, etc. In particular, this drawing shows the navigation engine's flow when using medical and pharmacy claims in combination with employer human resource records, with a cut-out for sorting and allocating the claims by both provider and treatment pattern, which is shown in FIG. 3, and a cut-out for determining an employee's healthy days and quality of life adjustment, which is shown in FIG. 6. As before, the navigation engine first organizes both the claims and the human resource records in tables with various headers that enable filtering, grouping and matching.

With the following exceptions, the flow when using claims and human resource records to determine the claims per healthy day with respect to employees is the same as when using only claims data. The perspective of what constitutes a good outcome, however, now shifts from the patient (or in this case, the employee) to that of the employer; and a good outcome for the employer is having the employee at work.

Total possible healthy days from an employer's perspective are the number of work days in the employer's year. For a typical employer, the number of work days in a year would be 240—five days per week (Monday through Friday) for the 52 weeks in a year, less a two-week (ten work day) vacation, less the ten national holidays recognized by the federal government ((5×52)−(2×5)−10=240). The navigation engine therefore uses 240 days as the default for the total possible healthy days over a one-year measurement period.

The navigation engine juxtaposes the dates of the claims for an employee's root diagnosis against the human resource attendance records and determines the days that the employee missed work due to that condition (e.g., days missed within a designated period before or after a claim are considered missed because of the condition)—these are the employee's non-healthy days. As before, the number of non-non-healthy days is risk-adjusted by dividing by the employee's risk score.

An additional feature that can be deployed by the navigation engine when using employer human resource records (but which is not required to be deployed), is to create a numerical job factor for each employee based on that employee's job demographics, which job factor is deployed with the risk scores. Elements that may weigh on the job factor include position rank, tenure, compensation (including hourly versus salary and part-time versus full-time), physical exertion that the job requires, time spent standing versus sitting, repetitive stress movements, and the emotional, mental and physical stress of the job.

Healthy days are then the total number of work days in the measurement period, 240 when the measurement period is a year, less the adjusted number of days that the employee misses work because of the medical condition (i.e., unhealthy days).

Continuing the example from above, take the PCP that treated ten patients during the year for diabetes (and assume that all ten were employees) with a total claims costs allocated to the PCP of $19,500. The average risk score of the ten employees was 1.300, so the PCP's total risk-adjusted claims cost was $15,000 ($19,500÷1.300=$15,000), or $1,500 per employee ($15,000÷10=$1,500). Now assume that the average job factor for these ten employees was 1.100, which would make the total risk and job adjusted costs $13,636 ($15,000÷1.100=$13,636), $1,363.60 per employee ($13,636÷10=$1,363.60). If the ten employees missed 280 days of work because of their diabetes (of the 300 non-healthy days from the previous example, 20 of those days occurred on non-work days), the risk-adjusted number of non-healthy days would be 215 (280÷1.300=215), or 21.5 per employee (215÷10=21.5), and then the job factor adjusted number of non-healthy days on top of that would be 195 (215÷1.100=195), or 19.5 per employee (195±10=19.5). The total healthy days would therefore be 2,205 ((10×240)−195=2,205), or 220.5 per employee (2,205÷10=220.5). Accordingly, the PCP's average claims per healthy day for treating these ten employees for diabetes would be $6.18 ($13,636÷2,205=$6.18 or $1,363.60÷220.5=$6.18). In other words, $6.18 is the average claims cost per day to keep these ten employees at work.

Figure 7:
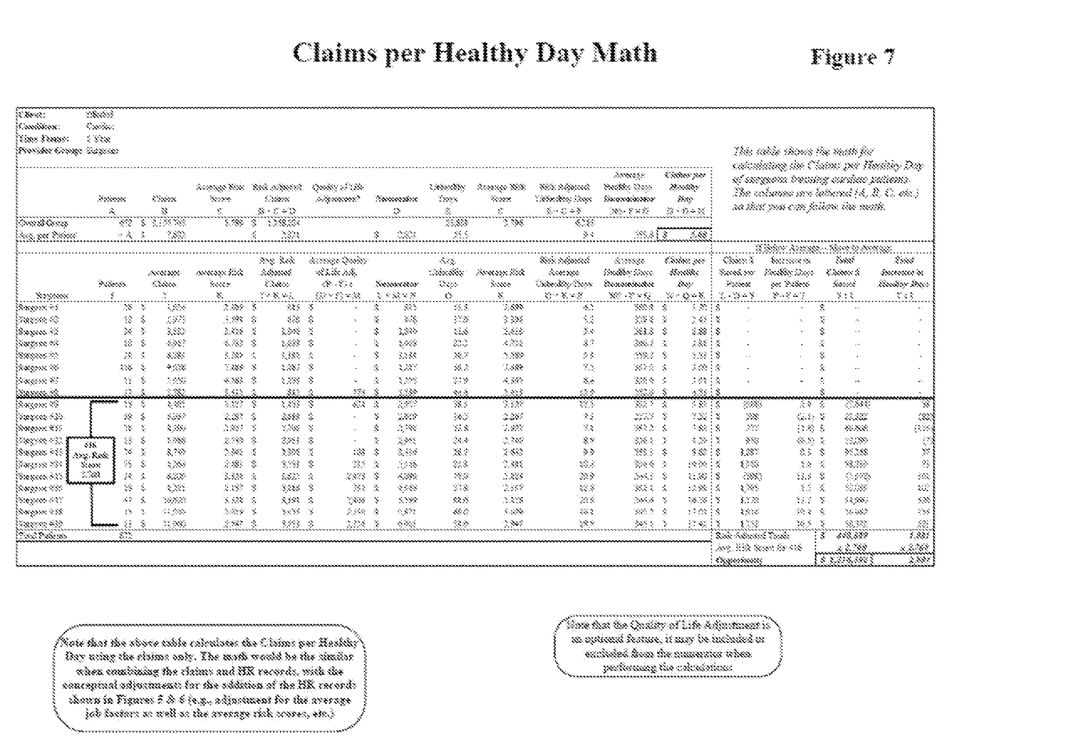
FIG. 7 shows the calculation of the claims per healthy day for a group of cardiac surgeons and the calculation of the claims per healthy day for each surgeon in that group (including the optional quality of life adjustment) using only the medical and pharmacy claims, and then the opportunity for claims savings and quality improvement by moving the patients going to worse than average surgeons to the average for the group.

FIG. 7 shows an example of calculating the claims per healthy day of 19 surgeons treating 672 cardiac patients using just the claims data. The columns in the table are lettered (A, B, C, etc.) to enable following the math. "Quality of Life Adjustment" applies only to providers whose average risk-adjusted unhealthy days are greater than the group average. The Quality of Life Adjustment includes the average value of excess unhealthy days in the numerator to provide greater separation between providers obtaining good results (more healthy days) from providers who are not. These Quality of Life dollars, however, are not included in the "Claims $ Saved per Patient" and the "Total Claims $ Saved" columns.

The middle of the table shows the averages for the 672 patients in the data set (Column A). The total medical and pharmacy claims related to the cardiac root diagnosis for these 672 patients was $5,155,743 (Column B), making the average per patient $7,672 ($5,155,743÷672=$7,672).

Risk scoring of the patients is required to normalize the results across the surgeons and level the playing field so that surgeons treating sicker patients are not penalized. The average risk score for the 672 patients was 3.796. Under the risk scoring system an individual of average health receives a risk score of 1.000, an individual healthier than average a risk score below 1.000 (the lower, the healthier), and an individual sicker than average a risk score above 1.000 (the higher, the sicker). When calculating this average, individuals with risk scores below 1.000 are assigned a normalized risk score of 1.000.

The claims are divided by the risk score to determine the risk-adjusted claims, a total of $1,358,204 and an average of $2,021 per patient (B÷C=D). This is the numerator in the calculation of the group's average claims per healthy day.

The group's total number of unhealthy days related to the cardiac diagnosis (i.e., days spent in the healthcare system or at home in a non-functional state) was 23,858, for an average of 35.5 unhealthy days per patient (Column E).

The unhealthy days are divided by the risk score to determine the risk-adjusted unhealthy days, a total of 6,285 days and an average of 9.4 unhealthy days per patient (E÷C=F).

The average number of unhealthy days of 9.4 are subtracted from the 365 days in a year to obtain the average number of healthy days per patient of 355.6 (365−F=G) This is the denominator in the calculation of the group's average claims per healthy day.

The numerator of $2,021 (Column D) is divided by the denominator of 355.6 healthy days (Column G) to obtain the group's average claims per healthy day of $5.68 (D÷G=H).

The balance of the table shows the calculations for each of the 19 surgeons treating the 672 patients. These surgeons are listed according to their average claims per healthy day, with the surgeon with the lowest average claims per healthy day on top, and the surgeon with the highest claims per healthy day on the bottom. The dark line between Surgeon #8 and Surgeon #9 separates surgeons doing better than average who are above the line (their average claims per healthy day is less than the group average of $5.68) from surgeons doing worse than average (their average claims per healthy day is more than the group average of $5.68).

For example, Surgeon #19 on the bottom row treated 21 patients (Column I). The average medical and pharmacy claims for each of those patients was $11,060 (Column J). Note that when allocating claims and unhealthy days to a provider the navigation engine allocates to them all the claims and unhealthy days for which they are responsible, both their direct claims and unhealthy days and the indirect downstream claims and unhealthy days from their referrals. This allows the engine to evaluate a provider's referral patterns, which is particularly useful when evaluating PCPs who often refer patients to specialists and surgeons. The average risk score of the 21 patients is 2.947 (Column K), making the average risk-adjusted claims per patient $3,753 (J÷K=L). This is the preliminary numerator in Surgeon #19's calculation of claims per healthy day. The quality of life adjustment discussed below will be added to it to obtain the final numerator.

Skipping Columns M and N for the time being, Column O gives Surgeon #19's average number of unhealthy days per patient as 58.6, which when divided by the average risk score yields a risk-adjusted average number of unhealthy days per patient of 19.9 (O÷K=P).

The average number of unhealthy days of 19.9 are subtracted from the 365 days in a year to obtain the average number of healthy days per patient of 345.1 (365−P=Q) This is the denominator in the calculation of Surgeon #19's average claims per healthy day.

Now going back to Columns M and N we calculate Surgeon #19's quality of life adjustment and add it to this surgeon's average risk-adjusted claims per patient to obtain the numerator in the claims per healthy day calculation. The quality of life adjustment provides further separation between those providers keeping their patients healthy (i.e., fewer unhealthy days) and those providers who are not (i.e., more unhealthy days). The quality of life adjustment is added to a provider's average risk-adjusted claims only when that provider's average risk-adjusted number of unhealthy days per patient exceeds the group's average number of risk-adjusted unhealthy days per patient. With respect to Surgeon #19, the quality of life adjustment is triggered because Surgeon #19's average risk-adjusted number of unhealthy days per patient of 19.9 (Column P) exceeds the group's average of 9.4 (Column F). Accordingly, Surgeon #19's number of excess unhealthy days per patient for purposes of the quality of life adjustment is 10.5 (19.9−9.4=10.5).

These 10.5 days are multiplied by the group's average risk-adjusted claims per unhealthy day, which is $215 (D÷F or $2,021÷9.4=$215), making the quality of life adjustment for Surgeon #19 the $2,258 shown in Column M (10.5× $215=$2,258). Note that the quality of life adjustment is on an average per patient basis, the same as the average risk-adjusted claims per patient shown in Column L.

Surgeon #19's average risk-adjusted claims per patient of $3,753 (Column L) is added to Surgeon #19's quality of life adjustment of $2,258 (Column M) to obtain the final numerator in the calculation of Surgeon #19's claims per healthy day of $6,011 (L+M=N).

Surgeon #19's numerator of $6,011 (Column N) is divided by this surgeon's denominator of 345.1 healthy days (Column Q) to obtain Surgeon #19's average claims per healthy day of $17.42 (N÷Q=R).

To quantify the magnitude of the opportunity for cost savings and care improvement, the remaining columns calculate what would happen if the patients going to worse than average surgeons (those below the line between Surgeon #8 and Surgeon #9) were moved to the average claims per healthy day of $5.68, not to one of the best surgeons on the top, but just to the average. Note that this example uses the group average to quantify this savings and care improvement opportunity. The engine can perform this determination using any base, such as moving patients to providers at the $75^{th}$ percentile or $90^{th}$ percentile. The average ($50^{th}$ percentile) is given as an example.

Continuing with Surgeon #19, the risk-adjusted claims that would be saved by moving that surgeon's patients to the average would be $1,732 per patient (L−D=S), and the increase in the number of healthy days would be 10.5 per patient (P−F=T). The totals for all 21 patients would be $36,372 (S×I) and 221 healthy days (T×I). Note that when calculating the claims savings the quality of life adjustment amount is excluded because it is only for ranking purposes.

There were a total of 416 patients going to surgeons who were worse than average (Surgeon #9-Surgeon #19), with an average risk score of 2.760. As shown in the bottom right corner, moving all 416 patients to the group average claims per healthy day of $5.68 would save $440,689 risk-adjusted dollars and increase the number of risk-adjusted healthy days by 1,081 days. As these are risk-adjusted dollars and days (they have been divided by the risk scores) to determine the real savings and care improvement opportunities requires multiplying them by the average risk score of 2.760 to gross them back up, resulting in a total savings opportunity of $1,216,302 and a total care improvement opportunity of 2,984 healthy days.

Figure 8:
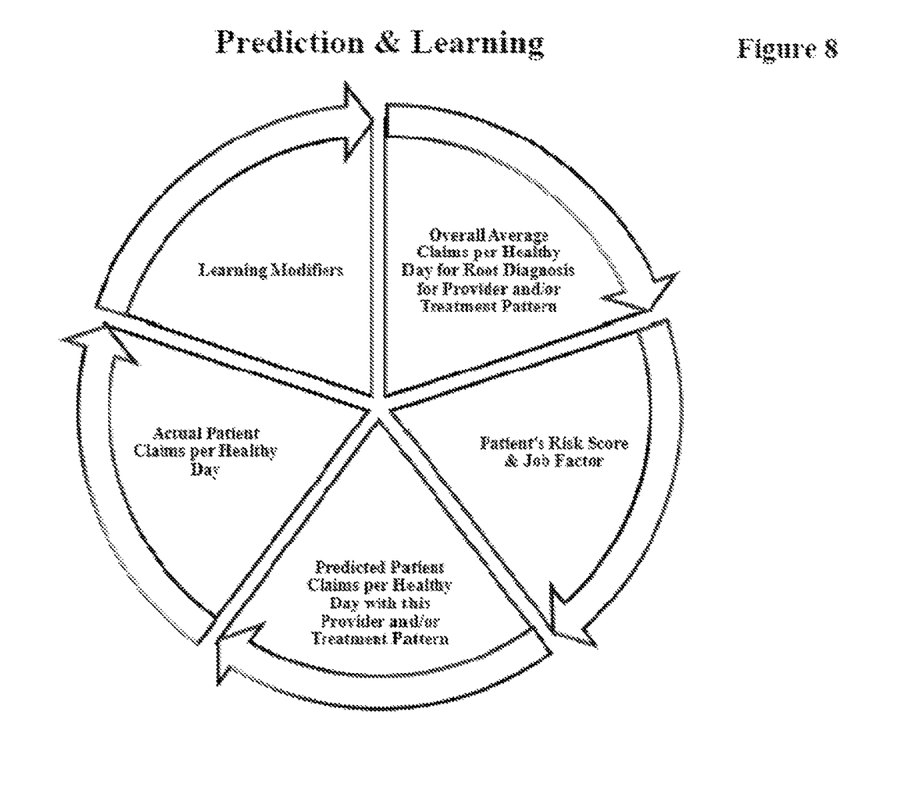
FIG. 8 shows the navigation engine's flow when predicting the claims per healthy day with respect to a particular patient or employee when going to a specific provider, or undergoing a specific treatment pattern, for a root diagnosis, and then the invention's neural network and machine learning feature. This drawing depicts predicting the outcomes achieved by physicians and treatment patterns only as an example. The invention can predict the outcomes for any Healthcare Item.

The invention now shifts from determining the historical average claims per healthy day of a Healthcare Item whose outcomes are being quantified when treating a root diagnosis, to predicting the claims per healthy day with respect to a particular patient. FIG. 8 shows this with respect to a patient going to a particular provider or undergoing a particular treatment pattern. This drawing shows the navigation engine's neural network and machine learning feature that predicts a quantified healthcare outcome-claims per healthy day. As an example, this drawing depicts predicting the outcome for a particular patient with a specified diagnosis seeing a particular provider or undergoing a particular treatment pattern for that diagnosis. The invention can predict the outcomes for anything, e.g., physicians and other providers, facilities, case managers, workers' compensation adjusters, healthcare treatment patterns and/or practices, healthcare plans and/or programs and provider networks etc.

The prediction is determined by: (1) taking the overall average claims per healthy day for that root diagnosis of the item, and (2) multiplying it by the risk score of the particular patient (1.000 for scores of 1.000 and below, the actual score for scores above 1.000), and then if an employee, (3)

multiplying that product by the employee's job factor (if the job factor feature has been deployed).

The prediction is then compared to the actual claims per healthy day achieved. This comparison can be performed on historical data when the actual claims per healthy day is known, or future data when the actual claims per healthy day is unknown, which would be the case when an individual is using the navigation engine to select a provider.

Regression analysis is then employed to modify the risk score and job factor as it affects the root diagnosis, with the modifying factors deployed as additional elements in the prediction formula. This analysis may address components or subsets of the risk score and job factor, such as whether a diabetic condition (a factor in the risk score) should be given more or less weight when predicting the total costs and/or healthy days for a particular root diagnosis.

The revised prediction is then compared to the actual claims per healthy day achieved, and the modifying factors adjusted in a "loop" of neural network and machine learning until the predicted claims per healthy day equals the actual claims per healthy day. Accordingly, the invention is a self-teaching outcome-based artificial intelligence navigation engine.

This detailed description is not intended to limit or represent an exhaustive enumeration of the principles disclosed. It will be apparent to those of skill in the art that numerous changes may be made in such details without departing from the spirit of the disclosed principles, and that the invention does not require all the features described above to be deployed for the invention to function.

The section headings herein are provided for consistency with the suggestions under 37 C.F.R. § 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

Moreover, the Abstract is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus, the following claims are hereby incorporated into the Detailed Description, with each claim standing on its own as a separate embodiment.

The invention claimed is:

1. A method in a computing environment for ranking Healthcare Items based on quantified outcomes they achieved, wherein said Healthcare Items comprise one or more of physicians and other healthcare providers, healthcare facilities, case managers, workers' compensation adjusters, healthcare treatment patterns and/or practices, healthcare plans and/or programs, and healthcare provider networks, the method comprising:

organizing patients' respective medical and/or pharmacy claims, made under one or more respective healthcare plans and/or programs, in tables with common identifiers linking each patient's claims;

identifying one or more distinct root diagnosis for each patient's claims;

accumulating all of the organized claims by a corresponding identified root diagnosis over an entire continuum of care for each identified root diagnosis, and then grouping those accumulated claims by a specified measurement period of time;

organizing eligibility files in tables for any applicable health plan or program for the organized claims;

determining through a common identifier whether each patient in the organized claims participated in one of the applicable healthcare plans or programs for the entirety of each measurement period;

determining a risk score for each patient using age, gender, health diagnoses, and drug prescriptions data contained in each patient's corresponding organized claims;

allocating to each physician that filed a at least one of the organized claims grouped with a patient's identified root diagnosis with both:
 (1) that physician's organized claims grouped with that patient's identified root diagnosis, and
 (2) all downstream claims from direct and indirect referrals of the patient made by that physician to other healthcare providers;

determining, per measurement period, risk-adjusted claims costs of each organized claim to treat a patient with a particular identified root diagnosis by:
 (1) combining all costs of a particular patient's claims and downstream costs allocated to a provider or other Healthcare Item when treating that particular root diagnosis of that particular patient, and
 (2) dividing those total combined costs by the particular patient's risk score;

determining, per measurement period, the total risk-adjusted claims costs of each Healthcare Item whose outcomes are to be quantified to treat patients with a particular identified root diagnosis by:
 (1) combining all the claims costs allocated to that Healthcare Item when treating that particular root diagnosis (including the downstream costs), and
 (2) dividing those combined costs by an average risk score of patients treated with that particular root diagnosis;

identifying from the organized claims all unhealthy days of each patient attributable to that particular root diagnosis during the measurement period, wherein unhealthy days comprise those days that the patient spends in the healthcare system or at home in a non-functional state relative to that patient's normal activities;

allocating to each physician that filed an organized claim grouped with a patient's identified root diagnosis both:
(1) unhealthy days of that patient attributable to that physician's claim(s), and
(2) unhealthy days of that patient attributable to all downstream claims from direct and indirect referrals of that patient made by that physician to other providers;

risk-adjusting the unhealthy days of that patient by dividing them by that patient's risk score;

determining healthy days for that patient by subtracting the risk-adjusted unhealthy days of that patient from the number of days in the measurement period;

determining, per measurement period, the claims per healthy day for each Healthcare Item whose outcome is being quantified when treating a particular patient with a particular identified root diagnosis by taking the risk-adjusted claims costs of that patient allocated to that Healthcare Item and dividing by that patient's number of healthy days, thereby providing that patient's claims per healthy day;

determining, per measurement period, an average claims per healthy day for each Healthcare Item whose outcome is being quantified when treating a particular identified root diagnosis by either:
dividing the total risk-adjusted claims costs allocated to that Healthcare Item when treating that particular diagnosis by the total healthy days of all patients treated for that particular root diagnosis, or alternatively,
dividing the average risk-adjusted claims per patient by the average number of healthy days per patient;

ranking the Healthcare Items whose outcomes are being quantified for each identified root diagnosis based on each Healthcare Item's overall average claims per healthy day over all specified measurement periods-from the best with lower or the lowest claims per healthy day to the worst with higher or the highest claims per healthy day;

presenting a navigational interface, via a system of visual searching on a computer screen, to a user searching for a Healthcare Item related to a particular root diagnosis, said ranked Healthcare Items for a particular root diagnosis, wherein said system of visual searching comprises:
presenting on a single computer screen the Healthcare Items related to the organized claims within corresponding functionally labeled circles connected in hierarchical order in the navigational interface;
organizing that order with a central circle branching off into a plurality of smaller circles, and from each of said plurality of smaller circles, branching off into a plurality of even smaller circles, with more detailed subsets of information related to a respective Healthcare Item presented in each circle as each of said circles hierarchically descend;
linking two or more of the circles with stems, wherein lengths and widths of the stems indicating the connectedness of the underlying data representing the Healthcare Items in respective circles;
displaying thumbnails of dashboards and/or reports available under a circle when the user hovers a cursor over one of the circles; and
in response to the user selecting a circle or a respective thumbnail of a dashboard and/or report, opening a new computer display screen from which the user can access said selected dashboards and/or reports.

2. The method of claim 1, further comprising:
comparing a Healthcare Item's average risk-adjusted unhealthy days to average risk-adjusted unhealthy days of the Healthcare Item's peer group, wherein said peer group comprises Healthcare Items whose outcome is being quantified and ranked, and determining an excess, if any, by which the Healthcare Item's average risk-adjusted unhealthy days exceed the peer group's average risk-adjusted unhealthy days;
valuing any such excess risk-adjusted unhealthy days at the peer group's average risk-adjusted claims cost per unhealthy day; and
adding the resulting valued amount to the Healthcare Item's average risk-adjusted claims as a "quality of life adjustment" when calculating the Healthcare Item's average claims per healthy day.

3. The method of claim 2, further comprising:
determining from the organized claims a risk score of a particular patient; and
predicting the claims per healthy day of each Healthcare Item when treating that particular patient for a particular root diagnosis by multiplying the risk score of that particular patient by an overall average claims per healthy day for that particular root diagnosis of the Healthcare Item.

4. The method of claim 3, further comprising:
comparing the predicted claims per healthy day for the particular patient with determined actual claims per healthy day;
employing regression analysis to modify the risk score and/or components or subsets thereof to provide a revised prediction of claims per health day, with modifying factors deployed as additional elements in the predicting step; and
comparing the revised prediction to the actual claims per healthy day, and then adjusting the modifying factors in a loop of neural network and machine learning until the predicted claims per healthy day equals the actual claims per healthy day.

5. The method of claim 1, further comprising filtering the ranking results displayed to the user, accessible via said opened computer display screen and in response to selection by the user, by variables comprising one or more of:
(1) root diagnosis,
(2) provider category,
(3) geographic proximity, and
(4) in-network versus out of network for the user.

6. The method of claim 1, further comprising filtering the ranking results displayed to the user based on type of user by:
(1) in response to the user's selection of being a plan provider, a provider network, an employer, or administrative user, displaying, via the navigational interface, all data, including the overall average claims per healthy day, for all the Healthcare Items whose outcomes are being quantified by root diagnosis;
(2) in response to the user's selection of being a primary care physician (PCP) or other physician, case manager, workers' compensation adjuster, or other healthcare provider making patient referrals or choosing from several health treatment patterns and/or practices, displaying, via the navigational interface:
(A) a list of surgeons, specialists, and healthcare institutions with an overall average claims per healthy day for a particular root diagnosis better than a designated threshold, and/or (B) possible health treatment patterns and/or practices for that particular root diagnosis with an overall average claims per healthy day for a particular root diagnosis better than a designated threshold; and (3) in response to the user's selection of being a patient or other individual seeking healthcare treatment, displaying, via the navigational interface:

(A) all providers with overall average claims per healthy day for a particular root diagnosis better than a designated threshold, and/or (B) overall average claims per healthy day for health treatment patterns and/or practices for that particular root diagnosis with overall average claims per healthy day better than a designated threshold.

7. The method of claim 1, further comprising sorting overall categories of the Healthcare Items whose outcomes are being ranked into sub-categories, and displaying sorted Healthcare Items in the sub-categories in the navigational interface, dashboards and/or reports.

8. The method of claim 7, wherein healthcare providers are sorted into four sub-categories comprising:
(1) primary care physicians (PCPs),
(2) non-surgeon specialists,
(3) surgeons, and
(4) healthcare institutions.

9. The method of claim 1, wherein each determined risk score is supplemented with social determinants of health, health plan and/or clinical data.

10. A non-transitory computer-readable medium having computer executable code for ranking Healthcare Items based on quantified outcomes they achieved, wherein said Healthcare Items comprise one or more of physicians and other healthcare providers, healthcare facilities, case managers, workers' compensation adjusters, healthcare treatment patterns and/or practices, healthcare plans and programs, and healthcare provider networks, said code when executed by one or more processors performs the process of:

organizing patients' respective medical and/or pharmacy claims, made under one or more respective healthcare plans and/or programs, in tables with common identifiers linking each patient's claims;

identifying one or more distinct root diagnosis for each patient's claims;

accumulating all of the organized claims by a corresponding identified root diagnosis over an entire continuum of care for each identified root diagnosis, and then grouping those accumulated claims by a specified measurement period of time;

organizing eligibility files in tables for any applicable health plan or program for the organized claims;

determining through a common identifier whether each patient in the organized claims participated in one of the applicable health plans or programs for the entirety of each measurement period;

determining a risk score for each patient using age, gender, health diagnoses, and drug prescriptions data contained in each patient's corresponding organized claims;

allocating to each physician that filed at least one of the organized claims grouped with a patient's identified root diagnosis with both:

(1) that physician's organized claims grouped with that patient's identified root diagnosis, and (2) all downstream claims from direct and indirect referrals of the patient made by that physician to other healthcare providers;

determining, per measurement period, risk-adjusted claims costs of each organized claim to treat a patient with a particular identified root diagnosis by:

(1) combining all costs of a particular patient's claims and downstream costs allocated to a provider or other Healthcare Item when treating that particular root diagnosis of that particular patient, and (2) dividing those total combined costs by the particular patient's risk score;

determining, per measurement period, the total risk-adjusted claims costs of each Healthcare Item whose outcomes are to be quantified to treat patients with a particular identified root diagnosis by:

(1) combining all the claims costs allocated to that Healthcare Item when treating that particular root diagnosis including the downstream costs, and (2) dividing those combined costs by an average risk score of patients treated with that particular root diagnosis;

identifying from the organized claims all unhealthy days of each patient attributable to that particular root diagnosis during the measurement period, wherein unhealthy days comprise those days that the patient spends in the healthcare system or at home in a non-functional state relative to that patient's normal activities;

allocating to each physician that filed an organized claim grouped with a patient's identified root diagnosis both:

(1) unhealthy days of that patient attributable to that physician's claim(s), and (2) unhealthy days of that patient attributable to all downstream claims from direct and indirect referrals of that patient made by that physician to other providers;

risk-adjusting the unhealthy days of that patient by dividing them by that patient's risk score;

determining healthy days for that patient by subtracting the risk-adjusted unhealthy days of that patient from the number of days in the measurement period;

determining, per measurement period, the claims per healthy day for each Healthcare Item whose outcome is being quantified when treating a particular patient with a particular identified root diagnosis by taking the risk-adjusted claims costs of that patient allocated to that Healthcare Item and dividing by that patient's number of healthy days, thereby providing that patient's claims per healthy day;

determining, per measurement period, an average claims per healthy day for each Healthcare Item whose outcome is being quantified when treating a particular identified root diagnosis by either:

dividing the total risk-adjusted claims costs allocated to that Healthcare Item when treating that particular diagnosis by the total healthy days of all patients treated for that particular root diagnosis, or alternatively, dividing the average risk-adjusted claims per patient by the average number of healthy days per patient;

ranking the Healthcare Items whose outcomes are being quantified for each identified root diagnosis based on each Healthcare Item's overall average claims per healthy day over all specified measurement periods- from the best with lower or the lowest claims per healthy day to the worst with higher or the highest claims per healthy day;

presenting a navigational interface, via a system of visual searching on a computer screen, to a user searching for a Healthcare Item related to a particular root diagnosis, said ranked Healthcare Items for a particular root diagnosis, wherein said system of visual searching comprises:
- presenting on a single computer screen the Healthcare Items related to the organized claims within corresponding functionally labeled circles connected in hierarchical order in the navigational interface;
- organizing that order with a central circle branching off into a plurality of smaller circles, and from each of said plurality of smaller circles, branching off into a plurality of even smaller circles, with more detailed subsets of information related to a respective Healthcare Item presented in each circle as each of said circles hierarchically descend;
- linking two or more of the circles with stems, wherein lengths and widths of the stems indicating the connectedness of the underlying data representing the Healthcare Items in respective circles;
- displaying thumbnails of dashboards and/or reports available under a circle when the user hovers a cursor over one of the circles; and
- in response to the user selecting a circle or a respective thumbnail of a dashboard and/or report, opening a new computer display screen from which the user can access said selected dashboards and/or reports.

11. The non-transitory computer readable medium of claim 10, wherein the performed process further comprises:
- comparing a Healthcare Item's average risk-adjusted unhealthy days to average risk-adjusted unhealthy days of the Healthcare Item's peer group, wherein said peer group comprises Healthcare Items whose outcome is being quantified and ranked, and determining an excess, if any, by which the Healthcare Item's average risk-adjusted unhealthy days exceed the peer group's average risk-adjusted unhealthy days;
- valuing any such excess risk-adjusted unhealthy days at the peer group's average risk-adjusted claims cost per unhealthy day; and
- adding the resulting valued amount to the Healthcare Item's average risk-adjusted claims as a "quality of life adjustment" when calculating the Healthcare Item's average claims per healthy day.

12. The non-transitory computer readable medium of claim 11, wherein the performed process further comprises:
- determining from the organized claims a risk score of a particular patient; and
- predicting the claims per healthy day of each Healthcare Item when treating that particular patient for a particular root diagnosis by multiplying the risk score of that particular patient by an overall average claims per healthy day for that particular root diagnosis of the Healthcare Item.

13. The non-transitory computer readable medium of claim 12, wherein the performed process further comprises:
- comparing the predicted claims per healthy day for the particular patient with determined actual claims per healthy day;
- employing regression analysis to modify the risk score and/or components or subsets thereof to provide a revised prediction of claims per health day, with modifying factors deployed as additional elements in the predicting step; and
- comparing the revised prediction to the actual claims per healthy day, and then adjusting the modifying factors in a loop of neural network and machine learning until the predicted claims per healthy day equals the actual claims per healthy day.

14. The non-transitory computer readable medium of claim 10, wherein the performed process further comprises filtering the ranking results displayed to the user, accessible via said opened computer display screen and in response to selection by the user, by variables comprising one or more of:
(1) root diagnosis,
(2) provider category,
(3) geographic proximity, and
(4) in-network versus out of network for the user.

15. The non-transitory computer readable medium of claim 10, wherein the performed process further comprises filtering the ranking results displayed to the user based on type of user by:
(1) in response to the user's selection of being a plan provider, a provider network, an employer, or administrative user, displaying, via the navigational interface, all data, including the overall average claims per healthy day, for all the Healthcare Items whose outcomes are being quantified by root diagnosis;
(2) in response to the user's selection of being a primary care physician (PCP) and other physician, case manager, workers' compensation adjuster, and other healthcare provider making patient referrals or choosing from several health treatment patterns and/or practices, displaying, via the navigational interface:
(A) a list of surgeons, specialists, and healthcare institutions with an overall average claims per healthy day for a particular root diagnosis better than a designated threshold, and/or
(B) possible health treatment patterns and/or practices for that particular root diagnosis with an overall average claims per healthy day for a particular root diagnosis better than a designated threshold; and
(3) in response to the user's selection of being a patient and other individual seeking healthcare treatment, displaying, via the navigational interface:
(A) all providers with overall average claims per healthy day for a particular root diagnosis better than a designated threshold, and/or
(B) overall average claims per healthy day for health treatment patterns and/or practices for that particular root diagnosis with overall average claims per healthy day better than a designated threshold.

16. The non-transitory computer readable medium of claim 10, wherein the performed process further comprises sorting overall categories of the Healthcare Items whose outcomes are being ranked into sub-categories, and displaying sorted Healthcare Items in the sub-categories in the navigational interface, dashboards and/or reports.

17. The non-transitory computer readable medium of claim 16, wherein healthcare providers are sorted into four sub-categories comprising:
(1) primary care physicians (PCPs),
(2) non-surgeon specialists,
(3) surgeons, and
(4) healthcare institutions.

18. The non-transitory computer readable medium of claim 10, wherein each determined risk score is supplemented with social determinants of health, health plan and/or clinical data.

* * * * *